United States Patent [19]

Hager et al.

[11] Patent Number: 5,210,249
[45] Date of Patent: May 11, 1993

[54] ORGANOSILICON COMPOUNDS CONTAINING S-ALKYLTHIOSULFATE GROUPS, PROCESSES FOR THEIR PREPARATION AND USE OF THE SAME

[75] Inventors: Rudolf Hager, Altötting; Bernward Deubzer, Burghausen, both of Fed. Rep. of Germany

[73] Assignee: Wacker-Chemie GmbH, Munich, Fed. Rep. of Germany

[21] Appl. No.: 944,579

[22] Filed: Sep. 14, 1992

[30] Foreign Application Priority Data

Oct. 24, 1991 [DE]   Fed. Rep. of Germany ....... 4135142

[51] Int. Cl.$^5$ .............................. C07F 7/08; C07F 7/10
[52] U.S. Cl. ...................................... 556/428; 556/429
[58] Field of Search ................................ 556/428, 429

[56] References Cited

U.S. PATENT DOCUMENTS

| | | | |
|---|---|---|---|
| 4,070,328 | 1/1978 | Homan et al. | 260/37 S B |
| 4,070,329 | 1/1978 | Homan et al. | 260/37 S B |
| 4,070,526 | 1/1978 | Colquhoun et al. | 428/537 |
| 4,133,939 | 1/1979 | Bokerman et al. | 428/447 |
| 4,537,595 | 8/1985 | Grüning et al. | 8/115.6 |
| 4,808,638 | 2/1989 | Steinkraus et al. | 522/24 |
| 4,895,917 | 1/1990 | Grüing | 556/428 X |

FOREIGN PATENT DOCUMENTS

| | | |
|---|---|---|
| 0401683 | 5/1990 | European Pat. Off. . |
| 3323881 | 7/1983 | Fed. Rep. of Germany . |
| 3735086 | 10/1987 | Fed. Rep. of Germany . |

OTHER PUBLICATIONS

Zur Chemie der Buntesalze, H. Distler, Angew. Chem., 79 (1967), p. 520.
S. F. Thames and L. H. Edwards, J. Heterocyclic Chemistry 5 (1968), pp. 115–117.
Journal of Organometallic Chemistry Library, Y. Goldberg, V. Dirnens and E. Lukevics, vol. 20, 1988, pp. 219 and 222.

*Primary Examiner*—Paul F. Shaver

[57] ABSTRACT

Organosilicon compounds which contain Bunte salt groups and contain units of the general formula $$R_a(R^1O)_b R^2{}_c SiO_{\frac{4-a-b-c}{2}} \qquad (I)$$

wherein R is a hydrogen atom or a monovalent organic radical, $R^1$ is a hydrogen atom or a monovalent organic radical, $R^2$ is a radical $-QS_2O_3M$, where Q is a divalent hydrocarbon radical and M is an alkali metal radical or optionally a substituted ammonium radical, a is 0, 1, 2 or 3, b is 0, 1, 2 or 3, and c is 0, 1, 2 or 3, processes for preparing the organosilicon compounds and their use are described.

10 Claims, No Drawings

ORGANOSILICON COMPOUNDS CONTAINING S-ALKYLTHIOSULFATE GROUPS, PROCESSES FOR THEIR PREPARATION AND USE OF THE SAME

The invention relates to organosilicon compounds having at least one S-alkylthiosulfate group which is bonded to silicon via carbon, a process for their preparation and the use of the same

BACKGROUND OF THE INVENTION

H. Distler in Angew. Chem. 79 (1967) 520 gives a review of the preparation methods and properties of organic compounds containing S-alkylthiosulfate groups, hereafter referred to as Bunte salt groups. These synthesis methods are essentially based on reaction of reactive compounds, such as alkyl halides, epoxyalkanes or alkenes, with an alkali metal thiosulfate in a polar medium. Since organosilicon compounds are insoluble or only slightly soluble in this medium, the described procedure cannot be applied without reservation to the preparation of organosilicon compounds containing Bunte salt groups.

Organosilicon compounds containing Bunte salt groups are already known. S. F. Thames and L. H. Edwards in J. Heterocyclic Chemistry 5 (1968) 115 describe, for example, the preparation of silanes containing Bunte salt groups by reaction of halogenoalkyltrimethylsilanes with aminoethanethiosulfuric acid or vinyltrimethylsilane with ethyleneimine. According to DE 33 23 881 A1 1 (Th. Goldschmidt AG; published on Jan. 10, 1985) and the corresponding U.S. Pat. No. 4,537,595 and DE 37 35 086 C1 (Th. Goldschmidt AG; published on Feb. 2, 1989) and the corresponding U.S. Pat. No. 4,895,917, organopolysiloxanes containing Bunte salt groups are prepared by reacting the corresponding epoxy-functional siloxanes with an alkali metal thiosulfate or ammonium thiosulfate. Since the epoxide ring is opened in this reaction, all the Bunte salt groups are bonded to the silicon over hydrocarbon spacers containing hydroxyl groups, which may have certain disadvantages in other applications or secondary reactions.

Therefore it is an object of the present invention to provide organosilicon compounds containing Bunte salt groups. Another object of the present invention is to provide a process for preparing organosilicon compounds containing Bunte salt groups.

SUMMARY OF THE INVENTION

The foregoing objects and others which will become apparent from the following description are accomplished in accordance with this invention, generally speaking, by providing organosilicon compounds which contain Bunte salt groups and have units of the general formula

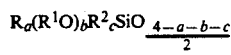  (I)

wherein R can be the same or different and represents a hydrogen atom or a monovalent organic radical, $R^1$ can be the same or different and represents a hydrogen atom or a monovalent organic radical, $R^2$ can be the same or different and represents a radical $-QS_2O_3M$, where Q is a divalent hydrocarbon radical and M is an alkali metal radical or optionally substituted ammonium radical, a is 0, 1, 2 or 3, preferably 1, 2 or 3, and more preferably 1 or 2, b is 0, 1, 2 or 3, preferably 0, 1 or 2, and more preferably 0 or 1, and c is 0, 1, 2 or 3, preferably 0, 1 or 2, and more preferably 0 or 1, with the proviso that the organosilicon compound contains at least one radical $R^2$ and the sum of a, b and c is less than or equal to 3.

The average value of a is preferably between 0.5 and 2.5, and more preferably between 1 and 2.4.

The average value of b is preferably between 0 and 2, and more preferably between 0 and 1.

The average value of c is preferably between 0.01 and 2, and more preferably between 0.1 and 1.

DESCRIPTION OF THE INVENTION

In the above unit formula, R is preferably optionally substituted hydrocarbon radicals having from 1 to 12 carbon atom(s), more preferably hydrocarbon radicals having from 1 to 6 carbon atom(s), and in particular R is the methyl radical.

Examples of radicals R are alkyl radicals, such as the methyl, ethyl, n-propyl, iso-propyl, n-butyl, iso-butyl, tert-hexyl radicals such as the n-hexyl radical; heptyl radicals, such as the n-heptyl radical; octyl radicals, such as the n-octyl radical and iso-octyl radicals, such as the 2,2,4-trimethylpentyl radical; nonyl radicals, such as the n-nonyl radical; decyl radicals, such as the n-decyl radical; and dodecyl radicals, such as the n-dodecyl radical; alkenyl radicals, such as the vinyl and the allyl radicals; cycloalkyl radicals, such as the cyclopentyl, cyclohexyl and cycloheptyl radicals and methylcyclohexyl radicals; aryl radicals, such as the phenyl and the naphthyl radicals; alkaryl radicals, such as o-, m- and p-tolyl radicals, xylyl radicals and ethylphenyl radicals; and aralkyl radicals, such as the benzyl radical and the α- and β-phenylethyl radicals.

The radical $R^1$ is preferably the hydrogen atom or optionally substituted hydrocarbon radicals having from 1 to 6 carbon atom(s), and more preferably the hydrogen atom and alkyl radicals having from 1 to 3 carbon atom(s), and in particular the methyl radical and the ethyl radical.

Examples of radicals $R^1$ are the examples having from 1 to 6 carbon atom(s) mentioned for the radical R.

The radical Q is preferably divalent hydrocarbon radicals having from 2 to 10 carbon atoms.

Examples of the radical Q are the ethylene, n-propylene, isopropylene, 1-n-butylene, 2-n-butylene, iso-butylene, tert-butylene, n-pentylene, iso-pentylene, neo-pentylene and tert-pentylene radicals, hexylene radicals, such as the n-hexylene radical, heptylene radicals, such as the n-heptylene radical, octylene radicals, such as the n-octylene radical, and iso-octylene radicals, such as the 2,2,4-trimethylpentylene radical, nonylene radicals, such as the n-nonylene radical, and decylene radicals, such as the n-decylene radical, as well as cycloalkylene radicals, such as cyclopentylene, cyclohexylene and cycloheptylene radicals and methylcyclohexylene radicals.

Preferably Q is the n-propylene radical.

Examples of the radical M are cations of the alkali metals, such as those of lithium, sodium, potassium, rubidium and caesium, and radicals of the formula

  (IV)

wherein $R^8$ can be the same or different and represents a hydrogen atom or a monovalent organic radical, such as, for example, the methyl, ethyl, n-propyl, iso-propyl, n-butyl, iso-butyl, n-pentyl, iso-pentyl, n-hexyl, n-heptyl, n-octyl, iso-octyl or benzyl radical.

The radical M is preferably sodium, potassium, ammonium, tetramethylammonium, tetrabutylammonium or benzyltriethylammonium, in which sodium and ammonium are the preferred M radicals.

Examples of radicals $R^2$ are —$(CH_2)_3S_2O_3Na$, —$(CH_2)_4S_2O_3Na$, —$(CH_2)_2C(CH_3)HS_2O_3NH_4$, —$(CH_2)_3S_2N(CH_3)_4$, —$(CH_2)_4S_2N(n-Bu)_4$, —$(CH_2)_5S_2O_3K$ and —$(CH_2)_2C(CH_3)_2CH_2S_2O_3Na$, where Bu is the butyl radical, in which —$(CH_2)_3S_2O_3Na$, —$(CH_2)_3S_2NH_4$, —$(CH_2)_4S_2O_3Na$ and —$(CH_2)_4S_2O_3NH_4$ are the preferred radicals and —$(CH_2)_3S_2O_3Na$ and —$(CH_2)_3S_2O_3NH_4$ are the more preferred radicals.

The organosilicon compounds of this invention, which contain Bunte salt groups, are preferably those having a molecular weight of 350 to 15,000.

Examples of organosilicon compounds of this invention, which contain Bunte salt groups are

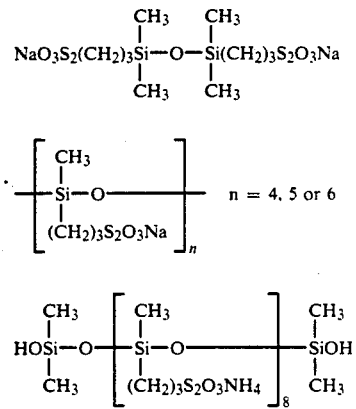

The organosilicon compounds of this invention, which contain Bunte salt groups, have the advantage that they contain no hydroxyl group adjacent to the Bunte salt group.

The present invention also relates to a process for preparing organosilicon compounds which contain Bunte salt groups, which comprises reacting at least one silane of the general formula

and/or a partial hydrolysate thereof, in which $R^3$ can be the same or different and is the same as R, $R^4$ can be the same or different and is the same as $R^1$, $R^5$ can be the same or different and represents the radical —Q'Y, where Q' is a divalent organic radical and Y is a halogen atom, d is 0, 1 or 2, preferably 1 or 2, and e is 1, 2 or 3, preferably 1 or 2, and more preferably 1, with the proviso that the sum of d and e is less than or equal to 3, and if appropriate at least one silane of the formula

and/or a partial hydrolysate thereof, in which $R^6$ can be the same or different and is the same as R, $R^7$ can be the same or different and is the same as $R^1$ and f is 0, 1, 2 or 3, preferably 1, 2 or 3, and more preferably 2 or 3, with at least one salt of thiosulfuric acid and water.

Q' preferably has one of the meanings discribed for Q; however, Q' can also represent divalent, substituted hydrocarbon radicals, although this is not preferred, the substituents preferably being insensitive to hydrolysis and undergoing no nucleophilic replacement with thiosulfate under the reaction conditions, such as, for example, hydrocarbons substituted by hydroxyl groups.

An example of the halogen atom Y is chlorine, bromine or iodine, in which Y preferably represents a chlorine atom.

Examples of the silane of formula (II) employed in the process of this invention are $(CH_3)_2(CH_3O)Si(CH_2)_3Cl$, $(CH_3)_2(CH_3CH_2O)Si(CH_2)_3Cl$, $CH_3(CH_3O)_2Si(CH_2)_3Cl$, $CH_3(CH_3CHO)_2Si(CH_2)_3Cl$, $(CH_3O)_3Si(CH_2)_3Cl$, $(CH_3CH_2O)_3Si(CH_2)_3Cl$, $(CH_3)_2(CH_3O)Si(CH_2)_4Br$, $CH_3(CH_3CH_2O)_2Si(CH_2)_3I$, $(CH_3CH_2CH_2O)_3Si(CH_2)_3Br$, $CH_3(CH_3O)_2Si(CH_2)_3I$ and $(CH_3CH_2CH_2O)_3Si(CH_2)_5Cl$, in which $(CH_3)_2(CH_3O)Si(CH_2)_3Cl$, $(CH_3)_2(CH_3CH_2O)Si(CH_2)_3Cl$, $CH_3(CHO_3)_2Si(CH_2)_3Cl$ and $CH_3(CH_3CH_2O)_2Si(CH_2)_3Cl$ are preferred and $(CH_3)_2(CH_3O)Si(CH_2)_3Cl$ and $CH_3(CH_3O)_2Si(CH_2)_3Cl$ are more preferred.

The silanes of formula (II) are commercially available comcompounds or can be prepared by known methods. Thus, for example, chloroalkyl-functional silanes can be prepared by platinum-catalyzed hydrosilylation of allyl chloride with the corresponding hydrido-functional silanes. Bromo- and iodo-functional silanes are available by an analogous method, but are preferably obtained from the corresponding chlorine compounds by exchange of the halogen atom. A reaction procedure with a phase transfer catalyst, such as is described by Y. Goldberg, V. Dirnens and E. Lukevics in "Journal of Organometallic Chemistry Library", Vol. 20, 1988, pages 219 to 222, is particularly advantageous here.

Examples of the silane of formula (III) employed, if appropriate, in the process of this invention are $(CH_3)_3SiOH$, $(CH_3)_3SiOCH_3$, $(CH_3)_3Si(OCH_2CH_3)$, $(CH_3)_2Si(OCH_3)_2$, $(CH_3)_2Si(OCH_2CH_3)_2$, $CH_3Si(OCH_3)_3$, $CH_3Si(OCH_2CH_3)_3$, $Si(OCH_2CH_3)_4$, $(CH_2CH)Si(CH_3)(OCH_3)_2$, $(C_6H_5)_3SiOH$ and $(CH_2CH)Si(CH_3)_2(OCH_3)$, in which $(CH_3)_3SiOH$, $(CH_3)_3SiOCH_3$, $(CH_3)_3Si(OCH_2CH_3)$, $(CH_3)_2Si(OCH_3)_2$ and $(CH_3)_2Si(OCH_2CH_3)_2$ are preferred and $(CH_3)_3SiOCH_3$ and $(CH_3)_2Si(OCH_3)_2$ are more preferred.

The silane of formula (III) is preferably employed in the process of this invention in amounts of from 0 to 1000% by weight, and more preferably from 0 to 500% by weight, based on the total weight of the silane of formula (II) employed.

The thiosulfuric acid salts employed in the process of this invention are preferably compounds which are soluble in water to the extent of at least 10% by weight at 100° C. under 1013 hPa, of the formula

in which M' can be the same or different and is the same as M, in which sodium thiosulfate and ammonium thiosulfate are preferred, and more preferably sodium thiosulfate.

Examples of thiosulfuric acid salts employed in the process of this invention are $Na_2S_2O_3$, $Na_2S_2O_3.5H_2O$, $(NH_4)_2S_2O_3$, $(NMe_4)_2S_2O_3$ and $(NMeH_3)_2S_2O_3$, where Me is the methyl radical.

The thiosulfuric acid salt is employed in the process of this invention in amounts of from 1 mol to 2 mols, preferably from 1 mol to 1.3 mol, and more preferably 1.1 mol, per mol of the radical Y in the silane of formula (II) employed in this invention. One mol of thiosulfuric acid salt per mol of radical Y of the silane formula (II) employed in this invention is in general sufficient to achieve a homogeneous reaction mass and a complete conversion of the radicals Y. However, complete conversion of the radicals Y is achieved faster with an excess of thiosulfate.

Water is preferably employed in the process of this invention in amounts of from 100 to 700% by weight, preferably from 150 to 350% by weight, based on the weight of silane of formula (II).

Furthermore a water-soluble organic solvent which is essentially inert to the reactants and reaction product can also be employed in the process of this invention, preferably in amounts of from 0 to 100% by weight, preferably from 0 to 50% by weight, based on the weight of water.

The thiosulfuric acid salt is preferably employed in the process of this invention as a mixture with water and if appropriate a water-soluble organic solvent.

Examples of suitable water-soluble organic solvents which are essentially inert to the reactants and reaction products are alcohols, such as methanol, ethanol, isopropanol and ethylene glycol, and dipolar aprotic solvents, such as ethylene glycol dimethyl ether, diethylene glycol dimethyl ether, 1,4-dioxane, N,N-dimethylformamide and tetrahydrofuran, and mixtures thereof, in which ethanol, isopropanol, ethylene glycol dimethyl ether and dimethylformamide are preferred and ethanol is more preferred.

In the process of this invention, the silane of formula (II), and if appropriate the silane of formula (III), the thiosulfuric acid salt, water and, if appropriate, the water-soluble organic solvent are mixed with one another in any desired sequence.

The process of this invention is preferably carried out at a temperature of from 20° C. to 110° C., preferably from 70° C. to 100° C., under a pressure preferably between 900 and 1100 hPa. However, the process of this invention can also be carried out under higher or lower pressures.

In a preferred embodiment of the process of this invention, the silane of formula (II), if appropriate as a mixture with the silane of formula (III), is mixed with a mixture of the thiosulfuric acid salt, the water and if appropriate the water-soluble organic solvent, and the components are stirred vigorously.

When the reaction of this invention is completed, the organosilicon compound containing Bunte salt groups can be isolated by processes which are well known in the art.

Preferably, when the reaction of this invention is completed, the reaction mixture is evaporated and the residue is extracted with a polar organic solvent which is essentially inert to the reaction products and can comprise up to 5% by weight, based on the weight of the organic solvent, of water. The evaporation is preferably carried out at a temperature of from 20° C. to 120° C., preferably from 50° C. to 100° C., under a pressure of from 0.01 to 50 hPa, and more preferably from 0.1 to 10 hPa. The polar organic solvent is preferably ethanol or isopropanol having a water content of from 2 to 5%. After the polar organic solvent has been evaporated off, the organosilicon compound containing Bunte salt groups is obtained as a solid or as a pasty or oily mass, depending on its composition.

The process of this invention has the advantage that organosilicon compounds containing Bunte salt groups can be prepared in a high yield in a relatively simple manner. The process of this invention has the added advantage that the starting substances are inexpensive and readily available.

If desired, the organosilicon compound containing Bunte salt groups which is obtained when the reaction of this invention is completed can be equilibrated with at least one organo(poly)siloxane (1), although this is not preferred. The equilibration can be carried out by processes known in silicon chemistry.

The organo(poly)siloxane (1) employed, with which the organosilicon compound prepared according to this invention is equilibrated, if appropriate, is preferably one consisting of units of the general formula

$$R^9_g(R^{10}O)_h SiO_{(4-g-h)/2} \qquad (VI)$$

in which $R^9$ can be the same or different and is the same as R, $R^{10}$ can be the same or different and is the same as $R^1$, g is 1, 2 or 3 and h is 0, 1 or 2, with the proviso that the sum of g and h is less than or equal to 3.

Examples of organo(poly)siloxanes (1) are linear organo(poly)siloxanes which contain terminal triorganosiloxy groups and have from 2 to 100 silicon units, linear organo(poly)siloxanes which contain terminal hydroxyl groups and have from 2 to 100 silicon units, and cyclic organo(poly)siloxanes which have from 3 to 12 silicon units.

The amounts and nature of the organo(poly)siloxane (1) employed in the equilibration stage optionally carried out in the process of this invention is determined primarily by the desired content of Bunte salt groups in the organosilicon compound produced in the equilibration stage and by the desired average chain length.

The equilibration is preferably carried out in the presence of catalysts which promote the equilibration. Examples of such catalysts are basic catalysts, such as, for example, alkali metal hydroxides, such as sodium hydroxide and potassium hydroxide, trimethylbenzylammonium hydroxide and tetramethylammonium hydroxide, as well as acid catalysts, such as, for example, sulfuric acid, phosphoric acid, trifluoromethanesulfonic acid, phosphorus nitride chlorides and acid catalysts which are solid under the reaction conditions, such as acid-activated bleaching earth, acid zeolites, sulfonated charcoal and sulfonated styrene/divinylbenzene copolymers. Basic catalysts are preferred, and of these KOH, tetramethylammonium hydroxide and trimethylbenzylammonium hydroxide are particularly preferred.

The equilibration catalyst is preferably used here in amounts of from 0.01 to 0.5% by weight, and more preferably from 0.02 to 0.1% by weight, based on the total weight of organosilicon compounds employed.

The equilibration optionally carried out is preferably carried out at from 80° C. to 150° C. under the pressure of the ambient atmosphere, that is, between 900 and 1100 hPa. If desired, however, higher or lower pressures can also be used.

The organosilicon compounds of this invention, which contain Bunte salt groups, can be further subjected to hydrolysis or condensation if they contain $OR^1$ groups, where $R^1$ is the same as above. Hydrolysis and condensation of organosilicon compounds containing organyloxy groups are already known in many instances. For example, the organosilicon compounds of this invention can be reacted with linear or cyclic organosilicon compounds containing hydroxyl groups, such as, for example, α,w-dihydroxydimethylpolysiloxane, in the presence of a catalyst, such as, for example, organotin compounds, titanium esters, zirconium esters, quaternary nitrogen bases and mineral acids, and, if appropriate, in the presence of solvents. The hydrolysis and condensation are preferably carried out at between 23° C. and 150° C., and more preferably between 60° C. and 120° C., under a pressure of between 900 and 1100 hPa.

The process of this invention can be carried out batchwise, semi-continuously or continuously.

The individual constituents employed in the process of this invention can in each case be one type of such constituents or a mixture of at least two types of such constituents.

The organosilicon compounds of this invention, which contain Bunte salt groups, can be employed for all purposes for which organosilicon compounds containing Bunte salt groups have been employed heretofore. In this context, reference may be made, to the publications already cited above, e.g., DE 33 23 881 A1 and DE 37 35 086 Cl. The possible uses mentioned therein are incorporated herein by reference. The organosilicon compounds of this invention, which contain Bunte salt groups, can thus be employed in processes for the surface treatment of inorganic and organic materials. For example, textile surfaces can be rendered permanently hydrophobic by a procedure in which the organosilicon compounds of this invention, which contain Bunte salt groups, are applied thereto and cross-linked by addition of sulfides at room temperature, to form disulfide bridges.

The possible uses of the organosilicon compounds of this invention, which contain Bunte salt groups, are mainly based on the one hand on their polarity and on the other hand on the high reactivity of the sulfur-sulfur bond present in the Bunte salt group. If the content of Bunte salt groups in the organosilicon compound of this invention is sufficiently high, the compounds dissolve in water to form a clear solution and reduce the surface tension of the water, since the organosilicon compounds of this invention, which contain Bunte salt groups, have a surfactant character due to their hydrophobic and hydrophilic molecular portions.

The organosilicon compounds of this invention, which contain Bunte salt groups, can also be employed in processes for the preparation of mercapto-functional organosilicon compounds.

Hydrolytic conversion of Bunte salt groups into mercapto groups, which is in general catalyzed by acid, is generally known, and proceeds in accordance with the equation:

radical-S$_2$O$_3^-$ + H$_2$O → radical-SH + HSO$_4^-$.

In this context, reference is made, for example, to A. Schöberl and A. Wagner: "Herstellung und Umwandlung von Mercaptanen und Thiophenolen" (Preparation and Conversion of Mercaptans and Thiophenols), in Houben-Weyl, Vol. 9, page 18f and the literature quoted therein.

The present invention further relates to a process for the preparation of mercapto-functional organosilicon compounds, which comprises reacting organosilicon compounds containing Bunte salt groups in the presence of water and acid.

The organosilicon compounds containing Bunte salt groups are preferably those containing units of formula (I).

The organosilicon compounds of this invention, which contain Bunte salt groups, having units of formula (I) which are preferably employed in the preparation of mercapto-functional organosilicon compounds are those which are prepared by the process of this invention by reacting a silane of formula (II), and if appropriate a silane of the formula (III), with a thiosulfuric acid salt and water.

Examples of the acid which may be employed are HCl, HBr, H$_2$S$_4$O, H$_3$PO$_4$, CH$_3$CO$_2$H, CH$_3$SO$_3$H, CF$_3$SO$_3$H and

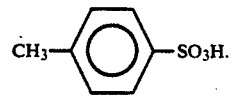

The acid employed in the process of this invention in the preparation of mercapto-functional organosilicon compounds is preferably HCl, H$_3$PO$_4$ or

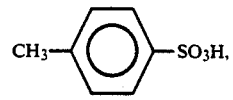

in which HCl is particularly preferably employed.

In the process of this invention for the preparation of mercapto-functional organosilicon compounds, the acid is preferably employed in amounts of from 1 to 75% by weight, and more preferably from 10 to 40% by weight, based on the total weight of organosilicon compound employed, which contains Bunte salt groups, of formula (I).

The acid is preferably employed in the process of this invention as a mixture with water in concentrations of preferably from to 50% by weight, and more preferably from 25 to 40% by weight, based on the weight of the mixture of water and acid. However, the acid can also be added in a higher concentration or in a pure form, if the reaction mixture already contains water, that is if, for example, the reaction mixture containing the Bunte salt synthesis has not been evaporated or has not been completely evaporated. The mixture of acid and water preferably additionally contains a water-soluble organic solvent in amounts of preferably from 100 to 2000% by weight, and more preferably from 800 to 1500% by weight, based on the weight of water.

Examples of water-soluble organic solvents which may be employed, if appropriate, are the examples mentioned above for solvents which may be employed, such as preferably methanol, ethanol, isopropanol and ethylene glycol, in which ethanol is the more preferred solvent.

Other substances, such as, for example, reducing agents, organo(poly)siloxanes having units of formula (VI) or silanes of formula (III), can additionally be employed in the process of this invention for the preparation of mercapto-functional organosilicon compounds.

It is preferred that a reducing agent be used, whereby the formation of disulfide as a side reaction can be largely avoided in the preparation of thiols from Bunte salt groups.

Examples of reducing agents which are employed, if appropriate, are zinc, iron, magnesium, sodium dithionite, hydroxylamine hydrochloride, hydrazinium sulfate and sodium phosphite, in which the preferred reducing agents are zinc, magnesium and hydroxylamine hydrochloride, with zinc being the more preferred reducing agent.

Examples of organo(poly)siloxanes having units of formula (VI) and silanes of formula (III) which are employed, if appropriate, are dimethylpolysiloxanes which have hydroxyl, methoxy or ethoxy end groups and an average chain length of from 2 to 150 silicon atoms, preferably an average chain length of from 5 to 100 silicon atoms and more preferably those having an average chain length of from 10 to 30 silicon atoms.

Preferred examples of organo(poly)siloxanes and silanes are hexamethyldisiloxane, 1,3-divinyl-1,1,3,3-tetramethyldisiloxane, trimethylmethoxysilane, dimethyldiethoxysilane and mixtures of these silanes and siloxanes.

The process of this invention for preparing mercapto-functional organosilicon compounds is preferably carried out at a temperature of from 30° C. to 110° C., and more preferably from 60° C. to 100° C. at a pressure of between preferably 900 and 1100 hPa. However, the process of this invention can also be carried out under higher or lower pressures.

The individual constituents employed in the process of this invention for the preparation of mercapto-functional organosilicon compounds can in each case be one type of such constituents or a mixture of at least two types of such constituents.

The process of this invention for the preparation of mercapto-functional organosilicon compounds has the advantage that the mercapto-functional organosilicon compounds are obtained in a simple manner and with high yields. This also applies if the silicon compounds of formula (I) containing Bunte salt groups which are employed are those in which all the silicon units contain Bunte salt groups, or the hydrolytic reaction is carried out in the presence of organosilicon compounds of units of the general formulas (III) and (VI).

In a preferred embodiment of the process of this invention for the preparation of mercapto-functional organosilicon compounds, in a 1st stage, at least one silane of the general formula (II) and/or a partial hydrolysate thereof and if appropriate at least one silane of formula (III) and/or a partial hydrolysate thereof is reacted with at least one thiosulfuric acid salt and water, after the 1st stage is completed and in a 2nd stage, the reaction mixture is completely or partly evaporated, as appropriate, and in a 3rd stage, the residue obtained in the 2nd stage is reacted with an acid, water and if appropriate other substances.

Addition of water in the 3rd stage can be omitted if the reaction mixture in the 2nd stage is not evaporated completely, and the amount of water required for the 3rd stage remains in the mixture.

The various stages of the process of this invention for the preparation of mercapto-functional organosilicon compounds can be carried out one after the other in one and the same reaction vessel, or in reaction vessels which are separate from one another. Preferably, the stages are carried out one after the other in one and the same reaction vessel. The process of this invention can be carried out batchwise, semi-continuously or continuously.

When the reaction of this invention is completed, the mercapto-functional organosilicon compounds of this invention can be isolated in a known manner. For example, the mercapto-functional organosilicon compounds can be isolated by adding a water-immiscible organic solvent, such as, for example, benzene, toluene, o-, m- or p-xylene, pentane or cyclohexane, preferably toluene, in which the mercapto-functional organosilicon compounds of this invention are readily soluble, to the reaction mixture. The amount of solvent is preferably from 10 to 150% by weight, and more preferably from 30 to 100% by weight, based on the total weight of water employed and, if appropriate, water-soluble organic solvent. The organic water-insoluble phase can be separated off from the aqueous phase. To isolate the mercapto-functional organosilicon compounds, the organic phase is evaporated at a temperature of preferably from 30° C. to 150° C. and more preferably from 80° C. to 120° C. at a pressure of from 1 to 100 Pa, and more preferably from 10 to 50 Pa. Compounds of low molecular weight, such as, for example, 1,3-bis(3-mercaptopropyl)-1,1,3-tetramethyldisiloxane, can be isolated by distillation.

If desired, the mercapto-functional organosilicon compounds of this invention can be equilibrated with organo(poly)siloxane (1) in the same manner as described above for the organosilicon compounds according to the invention, which contain Bunte salt groups. Sulfuric acid and compounds containing sulfuric acid, such as silicates broken down with sulfuric acid, or sulfonic acids, such as $CF_3SO_3H$, and in particular montmorillonite containing sulfuric acid, are preferably used as the equilibration catalyst.

The mercapto-functional organosilicon compounds of this invention can be employed for all purposes for which mercapto-functional organosilicon compounds have been or could have been employed heretofore. The mercapto-functional organosilicon compounds of this invention can be employed, for example, as cross-linking agents in thiol-ene systems. In this context, reference may be made, for example, to U.S. Pat. No. 4,808,638 (Loctite Corp., published on Feb. 28, 1989). Acrylate resins can be cured rapidly by heat with the aid of mercapto-functional organosilicon compounds under basic catalysis to form solid coatings on various substrates. In this context, reference may be made, for example, to EP 401 683 A (Wacker-Chemie GmbH; published on Dec. 12, 1990). Thiol-ene systems are suitable for the preparation of coatings on paper which repel tacky substances and can be cross-linked by high-energy radiation, in particular UV light, as described in U.S. Pat. No. 4,070,526 (Dow Corning Corp., published on Jan. 24, 1978). The mercapto-functional organosilicon compounds prepared by the process of this invention can also be polymerized in the absence of olefinic components to give sealing compositions or resins. In this context, reference is made, for example, to U.S. Pat. No. 4,070,329 (Dow Corning Corp., published on Jan. 24, 1978), U.S. Pat. No. 4,070,328 (Dow Corning Corp., published on Jan. 24, 1978) and U.S. Pat. No. 4,133,939 (Dow Corning Corp., published on Jan. 24, 1978).

The mercapto-functional organosilicon compounds of this invention can be used as an additive in adhesion promoters or polish formulations, and generally for modification of organopolysiloxanes.

In the following examples, all the viscosity data relate to a temperature of 25° C. Unless stated otherwise, the examples which follow are carried out under the pressure of the ambient atmosphere, that is, under about 1000 hPa, and at room temperature, that is at about 23° C., or at a temperature which is established when the reactants are brought together at room temperature without additional heating or cooling. Furthermore, all the parts and percentages are by weight, unless otherwise specified.

In the following examples, Me represents the methyl radical and Et represents the ethyl radical.

EXAMPLE 1

A mixture containing 20 g of 3-chloropropyldimethylmethoxysilane (0.120 mol) and 32.7 g of sodium thiosulfate 5-hydrate in 100 ml of water is rapidly stirred at 100° C. for 7 hours. The solution is then evaporated under a water pump vacuum at 60° C., and the solid which remains is extracted twice with 100 ml of boiling ethanol (contains 4% of water). The combined extracts are concentrated at 70° C. under a water pump vacuum and then heated thoroughly at 100° C. under an oil pump vacuum (20 Pa). About 27.6 g of colorless solid which contains about 95% of a disiloxane of the formula $O[Me_2Si(CH_2)_3S_2O_3Na]_2$ remain as the residue. The total yield of the reaction is thus 90%.

EXAMPLE 2

About 20 g of 3-chloropropylmethyldimethoxysilane (0.109 mol) are mixed with a solution containing 29.9 g of sodium thiosulfate 5-hydrate in 85 ml of water, and the mixture is heated at the boiling point, while stirring rapidly. After about 4 hours, the reaction mixture is homogeneous and the reaction is complete. The solution is evaporated under a water pump vacuum at 60° C. and the solid obtained is then extracted with ethanol (contains 4% of water) in a Soxhlet apparatus for 8 hours. After the solvent has been evaporated off under an oil pump vacuum (20 Pa) at 80° C., about 24.6 g of a colorless solid which contains more than 96% of units of the formula $$OSiMe(CH_2)_3S_2O_3Na$$

remain. This corresponds to a 91% yield.

EXAMPLE 3

A mixture containing 15 g of 3-chloropropylmethyldiethoxysilane (0.071 mol), 13 g of trimethylsilanol and 12.4 g of sodium thiosulfate in 50 ml of water and 20 ml of ethanol is boiled under reflux for 6 hours, while stirring rapidly. On cooling to room temperature, two phases separate. The phase having a lower specific gravity, which consists essentially of hexamethyldisiloxane, ethoxytrimethylsilane and ethanol, is discarded. The lower, aqueous phase is evaporated under a water pump vacuum at 60° C. The solid which remains is extracted three times with 50 ml of ethanol (water content 4%) each time, the combined extracts are then concentrated under a water pump vacuum and the residue is heated thoroughly at 80° C. under an oil pump vacuum (20 Pa). About 17.6 g of a white solid having the average composition $$Z-[OSiMe]_4-Z$$
$$|$$
$$(CH_2)_3$$
$$|$$
$$S_2O_3Na$$

are obtained, in which 90% of the stopper units Z are $Me_3SiO_{\frac{1}{2}}$ groups and 10% are $Me_2(EtO)SiO_{\frac{1}{2}}$ groups.

EXAMPLE 4

About 10 g of 3-chloropropylmethyldiethoxysilane (0.047 mol), 35 g of dimethyldiethoxysilane and 4.5 g of trimethylsilanol are added to a solution containing 8 g of sodium thiosulfate in 100 ml of water and 50 ml of ethanol, and the mixture is stirred rapidly at 100° C. for 6 hours. It is then cooled to room temperature, whereupon two phases form. The upper phase, which mainly consists of non-functional polydimethylsiloxanes and ethanol, is removed and discarded. The aqueous phase is concentrated under a water pump vacuum at 60° C., and the solid/oil mixture thus obtained is extracted twice with 50 ml of ethanol each time. After the combined extracts have been evaporated at 80° C. under 20 Pa, about 20.1 g of slightly cloudy, highly viscous oil having the average composition $$Me_3Si[OSiMe_2]_{28.2}[OSiMe]_{11.8}OSiMe_3$$
$$|$$
$$(CH_2)_3$$
$$|$$
$$S_2O_3Na$$

are obtained.

EXAMPLE 5

About 10 ml of a 37% solution of hydrochloric acid in water are added dropwise to a dispersion containing 9.6 g of organosilicon compound, which contains Bunte salt groups, from Example 1 and 2 g of zinc dust in 100 ml of boiling ethanol over a period of 30 minutes. When the addition of the acid is complete, the mixture is stirred under reflux for an additional 2 hours. The reaction mixture is then cooled to room temperature, and 50 ml each of water and toluene are added. After rapid mixing, the organic phase is separated off and concentrated first under a water pump vacuum and then under an oil pump vacuum (25 Pa) at 50° C. The colorless liquid which remains is subjected to fractional distillation under a pressure of 25 Pa, the main fraction (4.7 g) boiling at a temperature range of from 87° C. to 89° C. The resultant product is a mercapto-functional disiloxane of the formula $O[Me_2Si(CH_2)_3SH]_2$. Taking into account the Bunte salt content of the starting compound employed (about 95%), the yield is 89%.

EXAMPLE 6

A mixture containing 20 g of 3-chloropropyldimethylmethoxysilane (0.120 mol) and 19 g of sodium thiosulfate in 100 ml of water is boiled under reflux for 4 hours, while stirring vigorously, and is then evaporated at 80° C. under a water pump vacuum. About 150 ml of ethanol, 3 g of zinc dust and 97 g of a polydimethylsiloxane which contains hydroxyl end groups and has an average chain length of 15 silicon atoms are added to the solid residue. The mixture is heated to the boiling point and 10 ml of 37% hydrochloric acid in water are then metered in over a period of 15 minutes. The mixture is then stirred at the boiling point for an additional 2 hours. After cooling to room temperature, 70 ml each of toluene and water are added to the reaction mixture, and the organic phase having a lower specific gravity, is separated off and first concentrated under a water pump vacuum and then freed from all the volatile constituents under an oil pump vacuum at 100° C. under 10 Pa.

About 106.7 g of a colorless oil (viscosity: 39 mm²s⁻¹) having the average composition HS(CH₂)₃SiMe₂[OSiMe₂]₂₁.₄₀SiMe₂(CH₂)₃SH remain.

EXAMPLE 7

About 50 g of 3-chloropropylmethyldimethoxysilane (0.274 mol) and 43.5 g of sodium thiosulfate in 250 ml of water are stirred vigorously at the boiling point. After 3 hours, when the initially two-phase mixture is completely homogeneous and the reaction is completed, the reaction mixture is evaporated at 80° C. under a water pump vacuum. The residue is dispersed in 400 ml of ethanol together with 100 g of polydimethylsiloxane, which contains hydroxyl end groups and has an average chain length of 15 silicon atoms, about 14.5 g of hexamethyldisiloxane and 5 g of zinc dust. The mixture is heated to the boiling point, and 40 ml of 37% hydrochloric acid in water are added at this temperature over a period of 20 minutes. After the mixture has been boiled under reflux for an additional 2 hours, it is cooled to room temperature. The reaction product is worked-up in accordance with the procedure of Example 6, except that 250 ml each of water and toluene are added. After separation of the phases and evaporation of the organic phase, 141.2 g of a colorless oil (viscosity: 26.1 mm²s⁻¹), having the average composition represented by the following formula:

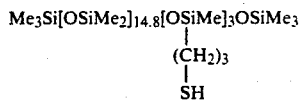

Me₃Si[OSiMe₂]₁₄.₈[OSiMe]₃OSiMe₃
                    |
                    (CH₂)₃
                    |
                    SH are obtained.

EXAMPLE 8

About 75 g of dimethylcyclotetrasiloxane and 2.5 g of a silicate which has been broken down with sulfuric acid (montmorillonite), as the equilibration catalyst (H₂SO₄ content: 8%), are added to 50 g of the mercapto-functional organopolysiloxane obtained from Example 7, and the mixture is stirred at 100° C. for 8 hours. It is then cooled to room temperature, and the catalyst is neutralized with 0.5 g of sodium bicarbonate, which is first moistened with 0.1 ml of water. After filtration and thorough heating of the filtrate at 110° C. under an oil pump vacuum (20 Pa), 120.2 g of a colorless oil having the average composition

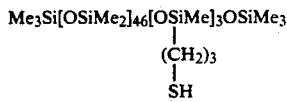

Me₃Si[OSiMe₂]₄₆[OSiMe]₃OSiMe₃
                    |
                    (CH₂)₃
                    |
                    SH are obtained.

EXAMPLE 9

About 50 g of 3-chloropropylmethyldimethoxysilane (0.274 mol) are reacted with 43.5 g of sodium thiosulfate to give poly-(3-thiosulfatopropylmethyl)siloxane, by a procedure similar to that described in Example 7. The evaporated product mixture is then mixed with 50 ml of ethanol, and then 5 g of zinc dust and 80 g of hexamethyldisiloxane are added and the mixture heated. As soon as the mixture boils, 50 ml of 37% hydrochloric acid in water are metered in over a period of 25 minutes, and the mixture is then boiled under reflux for an additional hour. After cooling to room temperature, a mixture containing water and toluene (250 ml of each) is added, and the organic phase is separated off and evaporated at 70° C. under 50 Pa. About 62.5 g of a colorless liquid (viscosity: 5.6 mm²s⁻¹), which consists essentially of a mixture of 1,1,1,3,5,5,5-heptamethyl-3-(3-mercaptopropyl)trisiloxane and 1,1,1,3,5,7,7,7-octamethyl-3,5-bis(3-mercaptopropyl)-tetrasiloxane remain. The average composition is represented by the formula

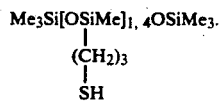

Me₃Si[OSiMe]₁.₄OSiMe₃
        |
        (CH₂)₃
        |
        SH

What is claimed is:

1. An organosilicon compound which contains Bunte salt groups and contains units of the general formula

$$R_a(R^1O)_bR^2_cSiO_{\frac{4-a-b-c}{2}} \quad (I)$$

wherein R is a hydrogen atom or a monovalent organic radical, R¹ is a hydrogen atom or a monovalent organic radical, R² is a radical —QS₂O₃M, where Q is a divalent hydrocarbon radical and M is an alkali metal radical or optionally a substituted ammonium radical, a is 0, 1, 2 or 3, b is 0, 1, 2 or 3, and c is 0, 1, 2 or 3 with the proviso that the organosilicon compound contains at least one radical R² and the sum of a, b and c is less than or equal to 3.

2. A process for preparing an organosilicon compound which contains Bunte salt groups, which comprises reacting at least one silane of the general formula

$$R^3_dR^5_eSi(OR^4)_{4-d-e} \quad (II)$$

and/or a partial hydrolysate thereof, in which R³ is a hydrogen atom or a monovalent organic radical, R⁴ is a hydrogen atom or a monovalent organic radical, R⁵ is the radical —Q'Y, where Q' is a divalent organic radical and Y is a halogen atom, d is 0, 1 or 2, and e is 1, 2 or 3, with the proviso that the sum of d and e is less than or equal to 3, and if appropriate at least one silane of the formula

$$R^6_fSi(OR^7)_{4-f} \quad (III)$$

and/or a partial hydrolysate thereof, in which R⁶ is a hydrogen atom or a monovalent organic radical, R⁷ is a hydrogen atom or a monovalent organic radical and f is 0, 1, 2 or 3, with at least one thiosulfuric acid salt and water.

3. The process of claim 2, wherein Y is a chlorine atom.

4. The process of claim 2, wherein the thiosulfuric acid salt is a compound which is soluble in water in an amount of at least 10% by weight at 100° C. under 1013 hPa, and is represented by the formula

$$M'_2S_2O_3 \quad (V)$$

in which M' is an alkali metal radical, an ammonium radical or a substituted ammonium radical.

5. The process of claim 2, wherein the thiosulfuric acid salt is employed in an amount of from 1 mol to 2 mols per mol of the radical Y in the silane of formula (II).

6. The process of claim 2, wherein the silane of formula (III) is employed in an amount of from 0 to 1000% by weight, based on the total weight of silane of formula (II).

7. A process for preparing a mercapto-functional organosilicon compound, which comprises reacting an organosilicon compound containing Bunte salt groups in the presence of water and an acid.

8. The process of claim 7, wherein the organosilicon compound containing Bunte salt groups is a compound having units of the formula $$R_a(R^1O)_bR^2_cSiO_{\frac{4-a-b-c}{2}} \tag{I}$$

wherein R is a hydrogen atom or a monovalent organic radical, $R^1$ is a hydrogen atom or a monovalent organic radical, $R^2$ is a radical $—QS_2O_3M$, where Q is a divalent hydrocarbon radical and M is an alkali metal radical or optionally a substituted ammonium radical, a is 0, 1, 2 or 3, b is 0, 1, 2 or 3, and c is 0, 1, 2 or 3 with the proviso that the organosilicon compound contains at least one radical $R^2$ and the sum of a, b and c is less than or equal to 3.

9. The process of claim 7, wherein in a 1st stage, at least one silane of the general formula $$R^3_dR^5_eSi(OR^4)_{4-d-e} \tag{II}$$

and/or a partial hydrolysate thereof, in which $R^3$ is a hydrogen atom or a monovalent organic radical, $R^4$ is a hydrogen atom or a monovalent organic radical, $R^5$ is the radical $—Q'Y$, where $Q'$ is a divalent organic radical and Y is a halogen atom, d is 0, 1 or 2, and e is 1, 2 or 3, with the proviso that the sum of d and e is less than or equal to 3, and if appropriate at least one silane of the formula $$R^6_fSi(OR^7)_{4-f} \tag{III}$$

and/or a partial hydrolysate thereof, in which $R^6$ is a hydrogen atom or a monovalent organic radical, $R^7$ is a hydrogen atom or a monovalent organic radical and f is 0, 1, 2 or 3, are reacted with at least one thiosulfuric acid salt and water, and after completion of the 1st stage, and in a 2nd stage the reaction mixture is completely or partially evaporated as appropriate, and in a 3rd stage, the residue obtained from the 2nd stage is reacted with an acid, water and if appropriate, other substances.

10. The process of claim 7, wherein the mercapto-functional organosilicon compound thus obtained is equilibrated with at least one organopolysiloxane containing units of the general formula $$R^9_g(R^{10}O)_hSiO_{(4-g-h)/2} \tag{VI}$$

in which $R^9$ is a hydrogen atom or a monovalent organic radical, $R^{10}$ is a hydrogen atom or a monovalent organic radical, g is 1, 2 or 3 and h is 0, 1 or 2, with the proviso that the sum of g and h is less than or equal to 3.

* * * * *